(12) United States Patent
Strong

(10) Patent No.: US 10,101,296 B2
(45) Date of Patent: Oct. 16, 2018

(54) MINI-GEL COMB

(71) Applicant: Bio-Rad Laboratories, Inc., Hercules, CA (US)

(72) Inventor: William Strong, El Cerrito, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 87 days.

(21) Appl. No.: 14/558,541

(22) Filed: Dec. 2, 2014

(65) Prior Publication Data

US 2015/0153306 A1    Jun. 4, 2015

Related U.S. Application Data

(60) Provisional application No. 61/910,853, filed on Dec. 2, 2013.

(51) Int. Cl.
*G01N 27/00* (2006.01)
*G01N 27/447* (2006.01)

(52) U.S. Cl.
CPC .............. *G01N 27/44704* (2013.01)

(58) Field of Classification Search
CPC .............................. G01N 27/44704
USPC ................................. 204/456, 620
See application file for complete search history.

(56) References Cited

U.S. PATENT DOCUMENTS

| | | | |
|---|---|---|---|
| 3,989,612 A | 11/1976 | Kragt et al. | |
| 4,294,684 A | 10/1981 | Serwer | |
| 5,116,483 A | 5/1992 | Lander | |
| 5,275,710 A | 1/1994 | Gombocz et al. | |
| 5,433,837 A | 7/1995 | Brunk et al. | |
| 5,449,446 A | 9/1995 | Verma et al. | |
| 5,512,146 A | 4/1996 | Brunk et al. | |
| 5,766,436 A | 6/1998 | Alam | |
| 5,993,627 A * | 11/1999 | Anderson ........ | G01N 27/44773 204/456 |
| 6,027,628 A * | 2/2000 | Yamamura ....... | G01N 27/44704 204/461 |
| 6,488,832 B2 | 12/2002 | Heller | |
| 6,936,150 B2 * | 8/2005 | Rooney .................. | C07K 1/26 204/456 |
| 2003/0015426 A1 | 1/2003 | Rooney et al. | |
| 2003/0032201 A1 | 2/2003 | Flesher | |
| 2007/0284250 A1 | 12/2007 | Magnant et al. | |

(Continued)

FOREIGN PATENT DOCUMENTS

| | | |
|---|---|---|
| WO | 2002/092200 A1 | 11/2002 |
| WO | 2013/180637 A1 | 12/2013 |
| WO | 2013/180639 A1 | 12/2013 |

(Continued)

OTHER PUBLICATIONS

The International Search Report and Written Opinion from International Application No. PCT/US2014/068230, dated Feb. 19, 2015.

(Continued)

*Primary Examiner* — Tamir Ayad
(74) *Attorney, Agent, or Firm* — Kilpatrick Townsend and Stockton LLP

(57) ABSTRACT

Molds for casting and retaining electrophoresis gel strips are provided, along with methods, kits, and systems for performing electrophoresis, electroelution, and/or electroblotting using these molds.

5 Claims, 6 Drawing Sheets

(56) References Cited

U.S. PATENT DOCUMENTS

2010/0126863 A1     5/2010  Stewart, Jr.

FOREIGN PATENT DOCUMENTS

| WO | 2013/180640 A1 | 12/2013 |
| WO | 2013/180641 A1 | 12/2013 |
| WO | 2013/180642 A1 | 12/2013 |
| WO | 2014/007720 A1 | 1/2014 |

OTHER PUBLICATIONS

U.S. Appl. No. 14/644,527, filed Mar. 11, 2015 by William Strong. (Unpublished.).
Extended European Search Report dated Oct. 28, 2016 in EP Application No. 14867041.7, 11 pages.

* cited by examiner

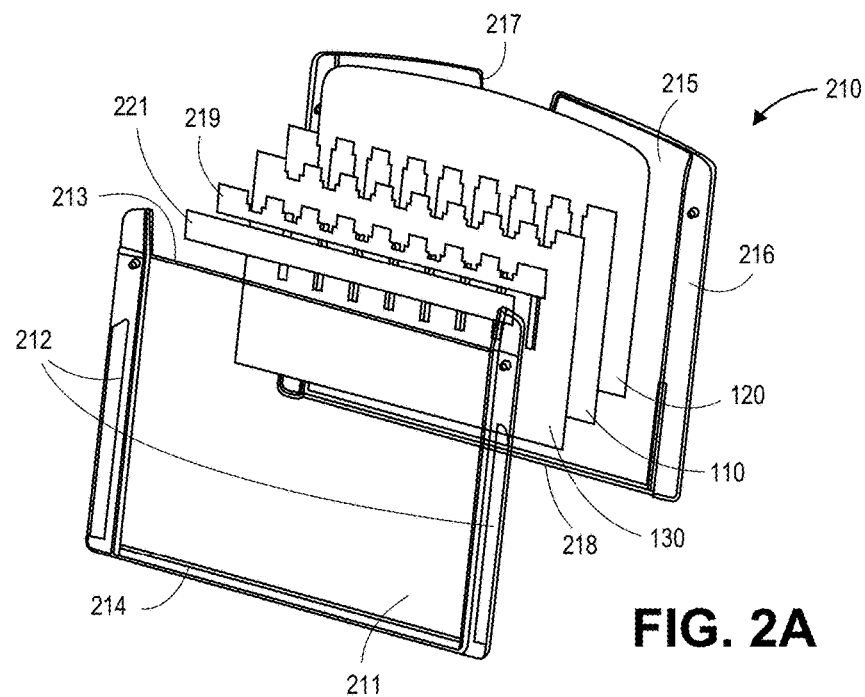
FIG. 2A
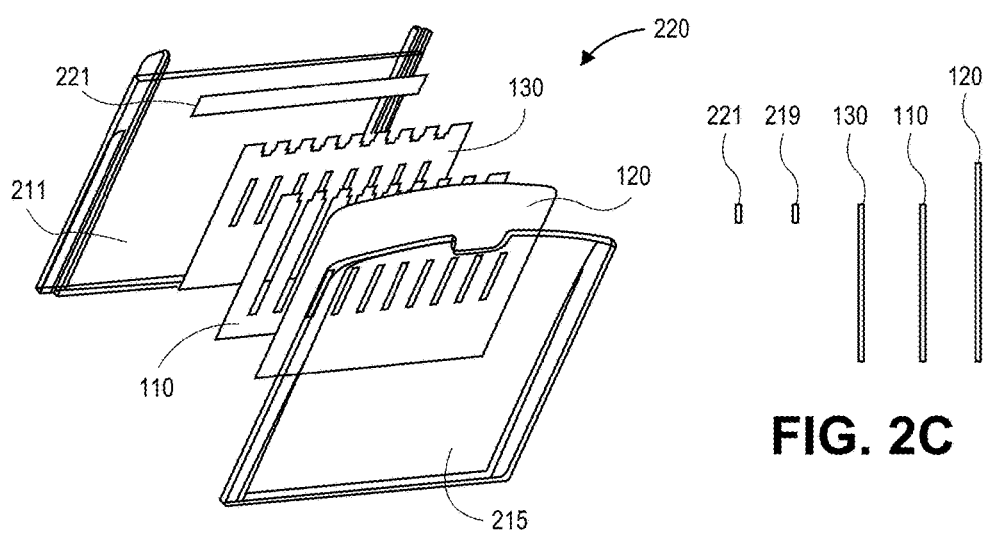
FIG. 2B
FIG. 2C

US 10,101,296 B2

MINI-GEL COMB

CROSS-REFERENCES TO RELATED APPLICATIONS

The present application claims priority to U.S. Provisional Application No. 61/910,853, entitled "MINI-GEL COMB" and filed Dec. 2, 2013, the entire contents of which are incorporated herein by reference for all purposes.

BACKGROUND OF THE INVENTION

Gel electrophoresis is a ubiquitous technique in molecular biology research, pharmaceutical manufacturing, and other enterprises. The technique can be used to analyze the content of a biological sample or purify sufficient quantities of macromolecules from the sample for later use. Protein mixtures, peptide mixtures, and mixtures of DNA, RNA, and fragments of DNA and RNA can all be subjected to gel electrophoresis, which separates molecules from each other on the basis of molecular weight, charge, or other characteristics.

Slab-shaped gels are often used when multiple separations must be performed simultaneously, because these gels can accommodate multiple samples in parallel lanes. A slab-shaped gel is typically prepared by filling a mold with a gel precursor, which can be a solution containing a chemical such as acrylamide or agarose. A "comb" is then inserted in the mold, with teeth of the comb protruding into the gel precursor. After the gel is cast, such as by inducing polymerization of a chemical in the precursor, or allowing the precursor to cool and solidify, the comb is removed, resulting in indentations in one end of the gel that are the negative shapes of the comb teeth. These indentations serve as wells in which samples can be loaded, and the starting points for lanes in the gel that each accommodate one sample.

Electrophoresis is performed by positioning a loaded slab gel, still retained in the mold or now placed in another supporting structure, between two electrodes. The electrodes are energized to opposite polarities, and the flow of current between the electrodes causes molecules from the samples to enter and migrate through the gel at different rates. This process is colloquially called "running the gel." The positions of the lanes along which the molecules migrate are determined by a number of factors, not all of which can be readily known or accounted for prior to running the gel. These factors include the positions of the wells into which the samples were loaded, the geometry of current flow (i.e., field lines) through the gel, and spatial variation in the composition of the gel. Uncertainty in the positions of lanes within a slab gel can be made worse by the impracticality of tracking molecules in real time as they migrate, and by the lack of physical segregation between lanes.

To harvest sample molecules from a slab gel, or characterize these molecules more extensively than is possible using electrophoresis alone, the techniques of electroelution or electroblotting are often performed after electrophoresis. These techniques require a current to be applied to the gel in a direction orthogonal to that used for electrophoresis, such that molecules arrayed in the gel migrate in a direction orthogonal to that achieved by electrophoresis and exit the gel. The molecules can then be collected on the surface of the gel (electroelution), or transferred to a membrane, where they can be reacted with binding partners and detected (electroblotting).

To prepare a slab gel for electroelution or electroblotting after electrophoresis, the gel typically must be removed from the structure in which electrophoresis was performed. This requires handling the gel, which is time consuming and can result in breakage, loss of portions of the samples, or loss of information about the positions of sample molecules within the gel. Because this information is anyway at best incomplete, due to uncertainty in where lanes of the gel are located, a membrane used for electroblotting must often cover a larger area of the gel than is occupied by molecules of interest. Detection of these molecules then requires larger amounts of binding partners and other reagents than would be necessary for a smaller membrane.

BRIEF SUMMARY OF THE INVENTION

Provided herein are molds for casting and retaining electrophoresis gel strips, methods of separating analytes and analyzing samples using the molds, and systems and kits for performing electrophoresis, electroelution, and electroblotting using the molds.

A mold for casting and retaining electrophoresis gel strips is provided. The mold includes: an array of elongated lane cavities, each lane cavity having a top end, a bottom end, and two or more sides, the lane cavities oriented parallel to each other; a matrix including at least one solid material and disposed along the sides of the lane cavities, the matrix separating the lane cavities from each other and from the space outside the mold; and a plurality of windows, where two windows are associated with each lane cavity and are disposed on opposite sides of the lane cavity, each window running lengthwise along the lane cavity and penetrating the matrix, thereby forming a passage from the lane cavity through the matrix to an adjacent lane cavity or the space outside the mold.

In some embodiments, the mold also includes a removable base sealing the bottom ends of the lane cavities from the space outside the mold.

In some embodiments, the mold also includes a removable window cover, the removable window cover contacting the matrix and aligned to at least one window, wherein the window cover prevents substances or current from passing through the window(s) to which the window cover is aligned.

In some embodiments, the mold also includes an adapter that includes a plurality of wells. The adapter can be disposed near the top ends of the lane cavities, such that the wells of the adapter are aligned with the lane cavities and are configured to facilitate the pouring of gel precursor into the lane cavities for casting gel strips or the loading of samples onto gel strips once cast.

In some embodiments of the mold, at least one lane cavity is tapered at the top end to facilitate pouring gel precursor into the lane cavity for casting a gel strip, or loading a sample onto the gel strip once cast. In these embodiments, the width of the lane cavity can be greater at the top end than the average width of the lane cavity. Alternatively, for a first portion of the matrix, the first portion separating the lane cavity from an adjacent lane cavity, the thickness of the first portion at the top end of the lane cavity is less than the average thickness of the first portion. Alternatively, for a second portion of the matrix, the second portion separating the lane cavity from the space outside the mold, the thickness of the second portion at the top end of the lane cavity is less than the average thickness of the second portion.

In some embodiments, the mold also includes a reservoir disposed near the top ends of the lane cavities and configured to retain liquid.

In some embodiments of the mold, the array of elongated lane cavities is one-dimensional, and the windows associated with each lane cavity form passages from the lane cavity through the matrix to the space outside the mold. The matrix can include a first solid material and a second solid material, the first solid material separating the lane cavities from each other and the second solid material separating the lane cavities from the space outside the mold. This first solid material can include a comb, which includes a plurality of teeth, and the lane cavities can include the spaces between the teeth. The second solid material can include two window plates bonded to opposite sides of the comb, with each window plate including at least one of the plurality of windows. The second solid material can also include at least two pieces, and the first solid material can be sandwiched between two pieces of the second solid material.

In some embodiments of the mold, the array of elongated lane cavities is two-dimensional and the lane cavities are arranged in the mold in rows and columns. The mold can be configured to be retained in a microtiter plate. The mold can also be configured to be broken into one or more sub-arrays of lane cavities, each sub-array corresponding to a row of lane cavities in the mold. In such a configuration, some of the plurality of windows can form internal passages between pairs of lane cavities in adjacent rows, such that breaking the mold into one or more sub-arrays bisects the internal passages, and the windows associated with the lane cavities of each sub-array form passages from the lane cavities to the space outside the sub-array.

In some embodiments of the mold, the array of elongated lane cavities is two-dimensional and the lane cavities are arranged in the mold in a circle.

The mold can also include one or more electrophoresis gel strips, where each gel strip is retained in one lane cavity, substantially fills the one lane cavity and the windows associated with the one lane cavity, and has a first end and a second end, the first end occurring near the top end of the one lane cavity, and the second end occurring near the bottom end of the one lane cavity.

A method of separating analytes of a sample is also provided. The method uses a mold that includes one or more electrophoresis gel strips. The method includes: loading a sample onto the first end of an electrophoresis gel strip retained in one lane cavity of the mold; and passing a current through the one lane cavity, between the first and second ends of the gel strip, thereby drawing the sample into the gel strip and separating analytes of the sample by electrophoresis.

The method can also include visualizing analytes of the sample in the gel strip. Analytes of the sample can be visualized through one of the windows associated with the one lane cavity.

Further provided is a method of analyzing a sample. This method uses an electrophoresis gel strip and a mold that includes a one-dimensional array of elongated lane cavities, where the windows associated with each lane cavity form passages from the lane cavity through the matrix to the space outside the mold. The method includes: loading a sample onto a first end of an electrophoresis gel strip retained in one lane cavity of the mold; passing current through the one lane cavity, between the first end and a second end of the gel strip, thereby drawing the sample into the gel strip and separating analytes of the sample by electrophoresis; removing any sealant or window covers over the windows associated with the one lane cavity; and passing current through the windows associated with the one lane cavity, in a direction orthogonal to that used for electrophoresis, thereby transferring analytes out the gel strip.

In some embodiments of this method, removing any sealant or window covers over the windows associated with the one lane cavity includes removing the mold from a cassette retaining the mold.

An additional method of analyzing a sample is also provided. This method uses an electrophoresis gel strip and a mold that includes a two-dimensional array of lane cavities, where the lane cavities are arranged in the mold in rows and columns, and the mold is configured to be broken into one or more sub-arrays of lane cavities, each sub-array corresponding to a row of lane cavities in the mold. The method includes: loading a sample onto a first end of an electrophoresis gel strip retained in one lane cavity of the mold; passing current through the one lane cavity, between the first end and a second end of the gel strip, thereby drawing the sample into the gel strip and separating analytes of the sample by electrophoresis; breaking the mold into one or more one-dimensional sub-arrays, where one one-dimensional sub-array contains the one lane cavity; removing any sealant or window covers over the windows associated with the one lane cavity; and passing current through the windows associated with the one lane cavity, in a direction orthogonal to that used for electrophoresis, thereby transferring analytes out the gel strip.

In some embodiments of this method, removing any sealant or window covers over the windows associated with the one lane cavity includes removing the sub-array from a cassette retaining the sub-array.

The methods of analyzing a sample can also include forming an electrophoresis gel strip in the one lane cavity of the mold. Such forming can involve submerging the mold in gel precursor, and allowing the gel strip to solidify in the one lane cavity. Forming can alternatively involve pouring gel precursor into the one lane cavity and allowing the gel strip to solidify.

The methods of analyzing a sample can also include placing a membrane near one of the windows associated with the one lane cavity, prior to passing current through the window, where the membrane is configured to receive analytes transferred out of the gel strip.

Further provided herein is a system for performing electrophoresis. The system includes: a cassette for retaining a mold as described above, a first electrode, and a second electrode. The first electrode is of opposite polarity from the second electrode, and is positioned near the top end of a lane cavity of the mold when the mold is retained in the cassette. The second electrode is positioned near the bottom end of the lane cavity when the mold is retained in the cassette.

An additional system is provided for performing electrophoresis and blotting using a mold with a one-dimensional array of elongated lane cavities, where the windows associated with each lane cavity form passages from the lane cavity through the matrix to the space outside the mold. The system includes a cassette for retaining such a mold, a first separation electrode, a second separation electrode, a motor, a first transfer electrode, and a second transfer electrode. In this system, the first separation electrode is of opposite polarity from the second separation electrode, and the first transfer electrode is of opposite polarity from the second transfer electrode. Furthermore, the first separation electrode is positioned near the top end of a lane cavity of the mold when the mold is retained in the cassette, and the second separation electrode is positioned near the bottom end of the lane cavity when the mold is retained in the cassette. The motor is configured to remove the mold from the cassette and place the mold in proximity to the first and second transfer electrodes, such that the first and second transfer electrodes are positioned on opposite sides of the lane cavity, near the windows associated with the lane cavity, after the mold has been removed from the cassette.

In some embodiments of these systems, the cassette is configured such that, when the mold is retained in the cassette, the cassette contacts the matrix of the mold and is aligned to the windows associated with the lane cavity, thereby preventing substances or current from passing through the windows associated with the lane cavity.

Finally, kits are provided. One kit includes a mold as described above, and a cassette for retaining the mold. The cassette contacts the matrix of the mold and is aligned to a window associated with at least one lane cavity, thereby preventing substances or current from passing through the window associated with the lane cavity.

Another kit also includes a mold as described above, and a cassette for retaining the mold. The cassette includes a wall contacting the matrix of the mold, wherein the wall comprises a solid portion and a through-hole, and the mold is configured to be shifted laterally within the cassette between a closed state and an open state. In the closed state, the solid portion is aligned to a window associated with at least one lane cavity, thereby preventing substances or current from passing through the window. In the open state, the through-hole is aligned to the window, thereby allowing substances or current to pass through the window.

Still another kit includes a mold with a removable window cover, and a motor configured to apply or remove the removable window cover.

BRIEF DESCRIPTION OF THE DRAWINGS

FIGS. 2A-C provide exploded views of the pieces of a mold according to one embodiment of the invention, and a cassette for retaining the mold.

DETAILED DESCRIPTION OF THE INVENTION

I. Introduction

Figure 1A:
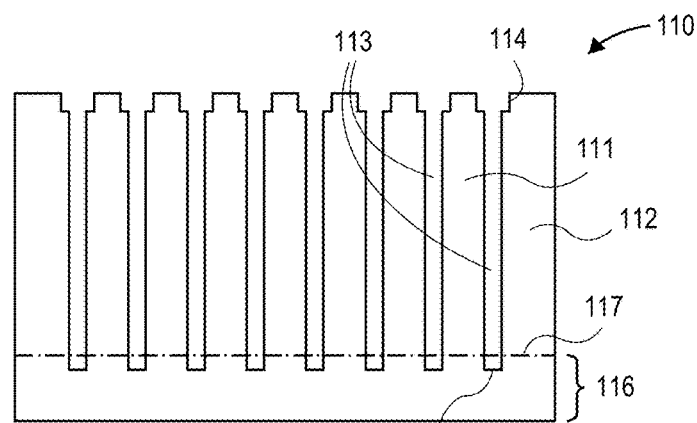
FIGS. 1A-C show a comb and two window plates that form the matrix of a mold, according to one embodiment of the invention.

It has now been discovered that a comb similar to that used for preparing sample wells in a slab gel can be used to prepare and retain gel strips. The gel strips occur between the teeth of the comb, each gel strip corresponding to one lane of a slab gel and accommodating one sample for electrophoresis. In some embodiments of the invention, the comb is part of a mold used to cast and retain gel strips in an array of lane cavities. Here, the teeth of the comb segregate the lane cavities from each other. In other embodiments, the mold does not include a comb, but includes other structures that carry out the same function. The mold can be open at the top and bottom of each lane cavity, and placed near electrodes, so that current can be passed through a gel strip retained in the lane cavity for electrophoresis. The mold also includes windows along the sides of each lane cavity through which current can be passed for electroelution or electroblotting. Current can thus be passed through the gel strip in orthogonal directions without having to open the mold or handle the gel strip. In some cases, the mold can be enclosed in a standard slab gel cassette during electrophoresis, with the walls of the cassette covering the windows of the mold and preventing current or sample molecules from passing through the windows. In some cases, membrane strips can be placed over the windows for electroblotting. Each membrane strip can cover one window and receive sample molecules from the gel strip located on the other side of the window. The membrane strip can be prepared or processed as appropriate for these particular sample molecules, and with smaller amounts of reagents than would be necessary for a membrane receiving molecules from multiple samples. In general, the mold allows electrophoresis to be performed in conjunction with electroelution or elecroblotting more conveniently than is possible with slab gels, with smaller amounts of samples and reagents, and at lower cost.

II. Molds

As described herein, the mold for casting and retaining electrophoresis gel strips is not required to incorporate a gel comb or similar structure, and is not in any way limited by such a structure. The mold minimally includes an array of elongated lane cavities, a matrix, and a plurality of windows. These features are described below, as are additional features that are included in some embodiments of the invention.

In the array of elongated lane cavities, each lane cavity has a top end, a bottom end, and two or more sides, and the lane cavities are oriented parallel to each other. (The present invention is not limited to embodiments in which each lane cavity is oriented perpendicularly to the ground. The terms "top and "bottom" are used for convenience and do not require that the top end of a lane cavity be located farther from the ground than the bottom end.) The number of lane cavities in the array can be, for example, 1, 2, 3, 4, 5, 6, 8, 10, 12, 15, 16, 18, 20, 24, 96, 384, or 1536. The lane cavities can be arrayed in the mold as desired, using any geometry. For example, the cavities can be placed next to each other in a row so that the top ends of the cavities appear disposed along a line. Alternatively, the cavities can be arranged in rows and columns so that the top ends of the cavities form a planar grid. The array can be one-dimensional or two-dimensional. As the terms are used herein, "one-dimensional" and "two-dimensional" refer to the arrangement of the lane cavities when viewed end-on. For example, in a one-dimensional array, a line perpendicular to the longitudinal axis of every lane cavity can be envisioned to connect all of the lane cavities. In a two-dimensional array, a plane perpendicular to the longitudinal axes of the lane cavities can be envisioned to intersect all of the lane cavities. Lane cavities can be spaced in the array as desired, with regular or irregular spacing, and any distance can be established between any two lane cavities.

The lane cavities are "elongated" in that the length of each lane cavity along its longitudinal axis, i.e. the distance between the top end and bottom end, is greater than the width of the lane cavity, as measured between any two points opposite each other on the sides of the lane cavity. The elongated geometry is necessary to achieve electrophoretic separation of sample molecules in a gel strip occupying the lane cavity, because the sample will typically spread out over the entire width of the lane cavity when loaded. This geometry reflects what is used in typical slab gel lanes, which are longer than they are wide. Lane cavities can have any cross-sectional shape (e.g., circular, elliptical, square, rectangular, triangular) and, subject to being elongated, any dimensions. A cylindrical lane cavity can have a length of 10 cm and a diameter of 1 cm, for example. A lane cavity with a rectangular cross-section can have a length of 5 cm and widths of 1 mm and 5 mm, for example. Other dimensions are provided below for specific embodiments.

The top and bottom ends of each lane cavity are sites where the lane cavity connects to the space outside the mold. These ends can be covered, however, for example to prevent contamination of gel slices cast in the lane cavities before samples are applied. In preferred embodiments, the top and bottom ends of a lane cavity define the direction of migration of samples during electrophoresis, with samples loaded onto the top end and migrating toward the bottom end. Accordingly, current passes between the top and bottom ends, and electrodes used in conjunction with the mold for electrophoresis are disposed near the top and bottom ends. In some embodiments, particularly where the lane cavities of the mold all have the same length, the top ends and/or bottom ends of the lane cavities are aligned with each other, so that samples loaded in adjacent lane cavities and migrating at the same rate migrate next to each other.

The sides of each lane cavity represent the boundaries of the lane cavity that are not defined by the top and bottom ends. Except along the windows, discussed below, the sides represent the interface between the lane cavity and the matrix in which the lane cavity is located. Accordingly, the matrix includes at least one solid material and is disposed along the sides of the lane cavities, separating the lane cavities from each other and the space outside the mold. The number of sides of each lane cavity is determined by its cross-sectional geometry. For example, a lane cavity with a rectangular cross-section has four sides. A lane cavity with a circular, elliptical, or other non-polygonal cross section is considered to have two sides, each corresponding to half of the cross-sectional perimeter, so that the two sides are opposite the cavity from each other.

The matrix of the mold is the solid or solids in which the lane cavities and windows (generally empty spaces) are formed. The matrix can be made up of a single, monolithic piece of solid material, or multiple pieces that are joined together. Pieces of the matrix can be prepared as desired, from plastic, ceramic, metal, or any other material, using any process, for example laser cutting, thermoforming, injection molding, blow molding, rotational molding, extrusion, or machining. When the matrix includes more than one piece, the pieces can be joined together as desired, using, for example, adhesives, solvent bonding, sonic welding, or thermal bonding.

The mold also includes a plurality of windows. Two windows are associated with each lane cavity and are disposed on opposite sides of the lane cavity, each window running lengthwise along the lane cavity and penetrating the matrix. In some embodiments of the mold, such as those where the lane cavities are arranged in a one-dimensional array, the windows form passages from the lane cavities to the space outside the mold. When the lane cavities retain gel strips, current can be passed through the windows to cause migration of molecules across the widths of the lane cavities, in a direction orthogonal to that used for electrophoresis. The windows can thus be used to transfer sample molecules out the gel strips by electroelution or electroblotting.

In other embodiments of the mold, the lane cavities are arranged in a two-dimensional array, and in some cases the windows form internal passages between adjacent lane cavities. These passages can result from the dense packing of the lane cavities in the mold and may not be intended for the transfer of materials between lane cavities. In these cases, the mold can be broken into sub-arrays of lane cavities, as is discussed below. Breaking the mold this way can break the internal passages between adjacent lane cavities, such that all windows of the sub-arrays then form passages to the space outside the mold. The windows of the sub-arrays can then be used for electroelution or electroblotting.

Windows in the mold can have any shapes or dimensions. For example, a window can run the entire length of the lane cavity with which it is associated, or only part of this length, and be as wide as the side of the lane cavity in which it is disposed, or less wide. In embodiments where the mold contains only a single lane cavity, a window can have approximately the same width as this lane cavity or the entire mold. A window can also be of uniform width, or have different widths along the length of the lane cavity (e.g., be narrowed or tapered near the bottom end of the lane cavity). A skilled artisan will recognize that a longer and wider window can lead to more efficient transfer or sample molecules by electroelution or electroporation, and transfer of molecules having a greater range of weights or charges. However, such a window, if left uncovered during electrophoresis, can also lead to greater distortion of the electric fields between the top and bottom ends of the lane cavity, and less predictable migration of molecules during electrophoresis. A longer or wider window also leaves a greater surface area of gel exposed to the outside of the mold. The end of the window closest to the top end of the lane cavity can be beveled or otherwise carved to discourage bubble formation in the window while casting a gel strip.

In some embodiments, the maximum width of a window is at most 1, 2, 5, 10, 20, 30, 40, 50, 60, 70, 80, 90, 95, or 99 percent of the maximum width of the lane cavity with which the window is associated. In some embodiments, the maximum width of a window is at least 1, 2, 5, 10, 20, 30, 40, 50, 60, 70, 80, 90, 95, or 99 percent of the maximum width of the lane cavity with which the window is associated. In some embodiments, the length of a window is at most 1, 2, 5, 10, 20, 30, 40, 50, 60, 70, 80, 90, 95, or 99 percent of the length of the lane cavity with which the window is associated. In some embodiments, the length of a window is at least 1, 2, 5, 10, 20, 30, 40, 50, 60, 70, 80, 90, 95, or 99 percent of the length of the lane cavity with which the window is associated.

The mold also includes a removable base in some embodiments to seal the bottom ends of the lane cavities from the space outside the mold. The base can be formed as part of one or more pieces of the matrix, or can be applied to the matrix after it is formed and assembled. In the latter case, the base can be applied at the time the matrix is manufactured or by the end-user of the mold. The base can prevent current from passing through the lane cavities and sample molecules from migrating through gel strips retained in the lane cavities by electrophoresis. The base is therefore removed before carrying out electrophoresis in most cases. The base is useful for preventing drying or contamination of gel strips before sample molecules are loaded. The base is also useful when casting gel strips in the mold, for preventing gel precursor from leaking out the bottoms of the lane cavities before it can solidify. The base can be made of any material and can have any structure. For example, the base can be a solid piece of plastic or a piece of film or tape covering the bottom ends of the lane cavities.

In some embodiments, the mold includes a removable window cover, which contacts the matrix and is aligned to at least one window. The window cover prevents substances or current from passing through the window(s) to which the window cover is aligned. The window cover is typically affixed to the outside of the matrix. Like the removable base, the window cover prevents drying or contamination of gel strips cast inside the mold, or leakage of gel precursor from the lane cavities during casting. The window cover can also prevent current or sample molecules from passing through the window during electrophoresis, and therefore can foster more uniform electric fields in the lane cavities and predictable migration of sample molecules. As desired, the window cover can be aligned to one window of the mold or multiple windows, for example all windows on one face of the mold. Similarly, one window cover or multiple window covers can be affixed to the mold. The window cover can be applied and removed from the mold as desired, using manual, motorized, or automated means. As discussed herein, window covers can be prepared from any convenient materials, such as plastics, polymer films, and adhesives, and can be rigid or flexible.

The mold can also include an adapter in some embodiments. The adapter can include a plurality of wells and be disposed near the top ends of the lane cavities, such that the wells of the adapter are aligned with the lane cavities. These wells can be configured to facilitate the pouring of gel precursor into the lane cavities for casting gel strips or the loading of samples onto gel strips once cast. Accordingly, the wells of the adapter can be angled or funnel shaped, to guide a vessel bearing gel precursor or pipette tips bearing samples to the lane cavities. The adapter can be useful for ensuring that gel precursor or samples are delivered to the appropriate lane cavities, and that spillage of such liquids near the top ends of the lane cavities is reduced or eliminated. The adapter can attach to the matrix of the mold, rest on top of the matrix, or be a part of the matrix, as desired. The wells can form sealed connections to the lane cavities, or simply be located near or serve as extensions of the top ends of the lane cavities. The adapter can have any shape or structure, be made of one piece or multiple pieces, and be made using any desired techniques or materials.

In some embodiments of the mold, at least one lane cavity is tapered at the top end to facilitate pouring gel precursor into the lane cavity for casting a gel strip, or loading a sample onto the gel strip once cast. This tapering can be engineered to facilitate the placement of an adapter, or can complement the function of an adapter. Alternatively, the top end of at least one lane cavity can be tapered to allow easier use of the mold in the absence of an adapter. Tapering can be achieved as desired, by widening the lane cavity at the top end and/or narrowing a portion of matrix adjacent to the top end. For example, the width of the lane cavity can be greater at the top end than the average width of the lane cavity. Or, for a first portion of the matrix separating the lane cavity from an adjacent lane cavity, the thickness of this first portion at the top end of the lane cavity can be less than the average thickness of the first portion. Or, for a second portion of the matrix separating the lane cavity from the space outside the mold, the thickness of this second portion at the top end of the lane cavity can be less than the average thickness of the second portion. As will be recognized, these possibilities are not necessarily mutually exclusive. To establish or characterize tapering, the widths or thicknesses of parts of the mold should be measured in a consistent manner along the length of a lane cavity, for example between the same two sides of the lane cavity. A lane cavity can be widened, or the thickness of a portion of the matrix can be reduced, during preparation of the matrix or afterward, using any desired technique.

The mold can also include a reservoir, which can be disposed near the top ends of the lane cavities and configured to retain liquid. When this liquid is an electrolyte-containing buffer, the reservoir can be used to facilitate electrophoresis. For example, the reservoir can be designed so that the buffer it retains submerges an electrode and also covers the top ends of the lane cavities. The buffer can thus serve to conduct current from the electrode to gel strips retained in the lane cavities, and further to an electrode of opposite polarity disposed near the bottom ends of the lane cavities. The reservoir is also useful for retaining liquids to facilitate the loading of samples onto the gel strips or prevent the drying or contamination of the gel strips, for example. For the reservoir to serve one of these purposes, the liquid capacity of the reservoir can be as large or small as desired. The reservoir can be formed out of the matrix of the mold (e.g., be an extension of the matrix) or attach separately to the matrix. Either way, the reservoir can be made of any material and have any shape or structure.

Any of the molds described herein can be provided with one or more electrophoresis gel strips. Each gel strip is retained in one lane cavity, substantially fills the one lane cavity and the windows associated with the one lane cavity, and has a first end and a second end, the first end occurring near the top end of the one lane cavity, and the second end occurring near the bottom end of the one lane cavity. The gel strips can be cast as desired, for example by pouring gel precursor into the lane cavities or submerging the mold in gel precursor. The gel strips can be cast simultaneously or at separate times. Casting can occur at the time the mold is manufactured, just prior to performing electrophoresis, or at any time in between. Any chemicals can be used in the gel precursor, for example acrylamide or agarose, and the gel strips can be induced to solidify as desired, for example by adding a cross-linker and/or catalyst to the precursor to induce polymerization, or by cooling the precursor. It will be recognized that gel strips having different compositions are useful for separating different kinds of samples.

In various places, the present specification describes or depicts molds that are configured for vertical electrophoresis. For example, the lane cavities in these molds, and the gel strips they contain, are shown oriented perpendicularly to the ground, such that sample molecules migrate through the gel strips from top to bottom. It should be noted, however, that all molds and associated apparatus described herein can have any orientation or be configured for any desired orientation. For example, the molds can be configured for horizontal electrophoresis. The present methods can be used to carry out electrophoresis with the direction of analyte migration being parallel to the ground or any other desired direction.

A. Molds Including One-Dimensional Arrays of Lane Cavities

The array of elongated lane cavities in the mold can have any geometry, and in some embodiments this array is one-dimensional. Here, the windows associated with each lane cavity form passages from the lane cavity through the matrix to the space outside the mold. A one-dimensional array is achieved, for example, by placing the lane cavities next to each other in a row in the matrix. So placed, and as a result of being oriented parallel to each other, the lane cavities all fall essentially in one plane. The passages formed by the windows through the matrix, or a path connecting the windows for one lane cavity (as would be traveled by current during electroelution or electroblotting), can then be oriented perpendicular to this plane. If the top ends of the lane cavities are aligned to each other, as is the case in some embodiments, then these ends can appear to fall along a line on one face or edge of the matrix. The same appearance can be obtained for the bottom ends of the lane cavities, and for both the top and bottom ends if the lane cavities have equal lengths.

Many constructions of the mold are consistent with a one-dimensional array of lane cavities. One such construction is discussed below, with reference made to FIGS. 1A-C, 2A-C, and 3A-C.

The matrix of the mold enclosing a one-dimensional array of lane cavities can include a first solid material and a second solid material in some embodiments. The first solid material separates the lane cavities from each other and the second solid material separates the lane cavities from the space outside the mold. It will be appreciated that the first and second materials can be the same material or different materials, and that, when different, these materials can be conveniently formed into separate pieces. The pieces can then be joined together to form the matrix. Forming the matrix piecewise can also be convenient when the first and second materials are the same.

FIG. 1A shows a piece of the matrix formed from a first solid material, which in this case is laser-cut plastic. The piece is a comb 110, which includes a plurality of teeth 111, 112. The lane cavities of the mold correspond to the spaces 113 between the teeth. Here, there are eight such spaces and the mold includes eight lane cavities, although any number of lane cavities can be present. In some embodiments, the number of lane cavities in a one-dimensional array equals the number of lanes found in a typical electrophoresis slab gel (for example, Mini-PROTEAN® Precast Gels, available from Bio-Rad Laboratories, Inc., Hercules, Calif., USA), or the number of teeth in a conventional gel comb used to prepare such a gel. The number of such lanes or teeth can be, for example, 1, 2, 3, 4, 5, 6, 8, 10, 12, 15, 16, 18, 20, or 24.

As shown, the lane cavities are tapered at the top ends due to indentations 114 in the teeth of the comb, which serve to widen the lane cavities at the top ends, as compared with the average width of the lane cavities, and reduce the thickness of the matrix between adjacent lane cavities, as compared with the average thickness of this part of the matrix. The bottom ends 115 of the lane cavities are sealed from the space outside the mold by a removable base, which is made up in part of the spine portion 116 of the comb. This portion can be broken along line 117 to expose the bottom ends of the lane cavities. Breaking can be done after gel strips have been formed in the spaces 113, for example just prior to electrophoresis.

Figure 1B:
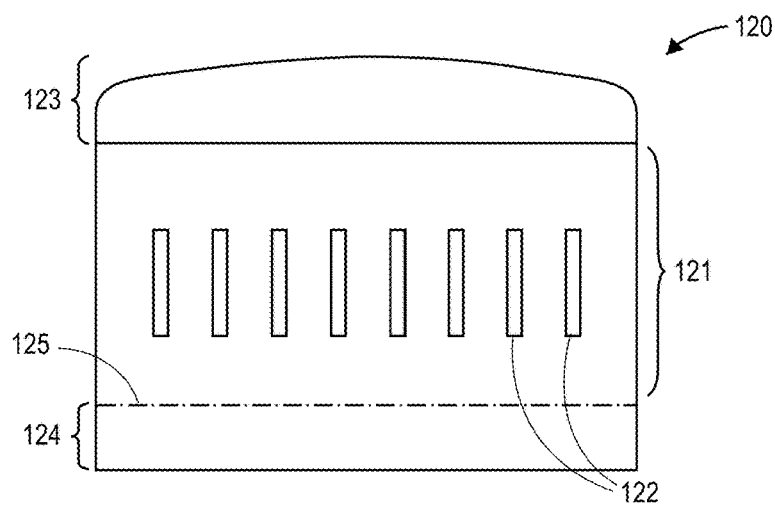
Figure 1C:
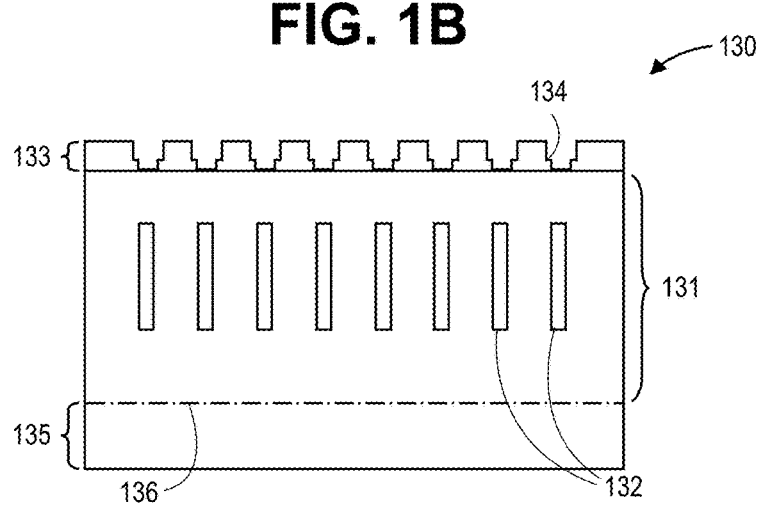

The window plates 120 and 130, shown in FIGS. 1B and 1C, respectively, are formed of the second solid material of the matrix. Here, the second solid material is also laser-cut plastic. Portions 121, 131 of the window plates are sized to be bonded to opposite sides of the comb 110, thereby forming two sides of each lane cavity, in addition to the two formed by the teeth adjacent to the lane cavity. Because the teeth of the comb have roughly uniform and equal thickness, in the direction perpendicular to a plane containing the teeth and spine, each lane cavity has a roughly rectangular cross-section. Each window plate includes at least one window 122, 132, and as shown includes windows equal in number to the spaces 113 between the teeth of the comb. The windows are aligned to the lane cavities defined by these spaces 113, but are not as wide as the lane cavities (2 mm vs. 3 mm) and do not run the entire length of the lane cavities. Accordingly, when gel slices are retained in the lane cavities, electroeluting or electroblotting affects mainly sample molecules located in those portions of the gel slices that are between the windows.

The window plates include bottom portions 124 and 135, which make up parts of the removable base of the mold. These portions align with the spine portion 116 of the comb and can be broken away from the window plates along lines 125 and 136. This can occur at the same time the spine portion is broken away from the comb, as may be convenient if the window plates are already bonded to the comb, or at another time. As shown, window plate 130 includes wells 133 that form part of an adapter for the mold. The wells include indentations 134 that geometrically match the indentations 114 in the teeth of the comb. In some embodiments, the wells 133 are omitted.

Window plate 120 also includes a handle portion 123, extending above the top ends of the lane cavities, that facilitates manual manipulation of the mold. The handle portion can include printed markings, in the form of, for example, text, a barcode, or symbols, optionally in multiple colors, that can be associated with information such as the composition of gel strips cast in the lane cavities, the expiration date of these gel strips, the types of samples to be loaded onto the gel strips, or the lot number of the mold. Printed markings on the handle portion can also be used to align the mold with a membrane or membrane strips for electroblotting.

Bonding the comb to the window plates serves to sandwich the comb between the window plates. This arrangement exemplifies embodiments of the invention where the second solid material of the matrix includes at least two pieces, and the first solid material is sandwiched between two pieces of the second solid material. As used herein, "sandwich" has the conventional meaning of placing one or more objects between two other objects in layers or in a stack. In addition to sandwiching together pieces of the mold, the mold can be conveniently sandwiched between other pieces of apparatus to facilitate electrophoresis and electroelution/electroblotting workflows.

In some embodiments of the invention, the mold is included in a kit with a cassette for retaining the mold. An example of such a cassette is shown in FIGS. 2A-C and 3A-C. The cassette includes two walls 211, 215 that can be joined to each other along their edges 212, 216. The comb 110 and window plates 120, 130 of the mold can be sandwiched together and enclosed between the walls of the cassette, with the layerings 210, 220 shown in FIGS. 2A and 2B. The resulting cassette can be used to prepare gel strips in the lane cavities of the mold and run samples on the gel strips using conventional electrophoresis chambers.

The walls of the cassette can be made of any materials and prepared as desired, but as shown are made of transparent injection-molded plastic. The walls can be joined together as desired, for example using welding, chemical bonding, or interlocking teeth or hooks along the edges 212, 216. Upon joining, the pressure exerted on the mold pieces by the cassette walls can be sufficient to hold these pieces together, with lane cavities exhibiting good sealing for casting gel strips or carrying out electrophoresis. Accordingly, in some embodiments, it is not necessary to bond together the comb and window plates prior to placement in the cassette. In other embodiments, however, such bonding is used to keep the mold intact, and resilient to manipulation, after it is removed from the cassette. As shown, pieces of the mold were bonded together by placing adhesive on both sides of the comb 110 that come into contact with the window plates 120, 130. The mold can be assembled at the time it is enclosed in the cassette, or can be assembled first and then inserted into the cassette, with the walls of the cassette already joined together.

The bottom edges 214, 218 of the cassette walls are designed such that the bottom of cassette can remain open to the outside upon joining the cassette walls together. This arrangement allows gel precursor to enter the lane cavities of the mold when the cassette is submerged or dipped into precursor, provided that the removable base of the mold has been removed beforehand. By submerging the cassette in gel precursor and then allowing the gel precursor to harden, gel strips can be cast in the lane cavities. During electrophoresis, the open bottom of the cassette also allows the free flow of current through the gel strips to or from an electrode disposed below the cassette.

An alternative method of casting gel strips involves sealing the bottom edges of the cassette with tape and filling the cassette with gel precursor. Inserting the mold into the cassette, with the removable base removed, displaces some of the precursor and allows gel precursor to fill the lane cavities of the mold. After the gel precursor has solidified, the tape can be removed for electrophoresis.

In some embodiments, the cassette contacts the matrix of the mold and is aligned to a window associated with at least one lane cavity. The cassette thereby prevents substances or current from passing through the window associated with the lane cavity, for example during electrophoresis. In the particular configuration shown in FIGS. 2A and 2B, each cassette wall contacts one window plate and is thus aligned to all windows of the window plate. By sealing the windows, the cassette serves as a window cover and makes separate removable window covers unnecessary. The cassette also provides a convenient route to conducting electrophoresis followed by electroelution or electroblotting using the mold. First, electrophoresis can be carried out with the mold enclosed in the cassette, using a standard apparatus that keeps the top and bottom ends of the cassette (and thereby the lane cavities and gel strips) submerged in buffer and in proximity to electrodes. Then, the mold can be removed from the cassette, thereby unsealing the windows, and the mold can be placed between plate electrodes to transfer sample molecules out of the gel strips.

In other configurations of the cassette not shown in FIGS. 2A-C and FIGS. 3A-C, through-holes are cut into the cassette walls that are similar in size, shape, and spacing to the windows 122, 132 of window plates 120, 130. The through-holes cut into a cassette wall can be equal in number to the windows in the adjoining window plate, or there can be more or fewer through-holes than windows, as desired. The through-holes occur opposite each other when the two walls of the cassette are joined together. When the mold is initially inserted in the cassette, the windows are laterally offset from the through-holes, and the solid portions of the cassette walls between the through-holes seal the windows. This position of the mold within the cassette is referred to as the "closed state". In this state, electrophoresis can be carried out inside the mold as discussed above and is unaffected by the through-holes. Subsequently, however, the mold can be slid or shifted laterally within the cassette so that the windows and through-holes align. This position of the mold within the cassette is referred to as the "open state". In this state, the windows of the mold and the through-holes in the cassette walls together provide direct passages from the gel strips to the space outside the cassette. The mold can then be placed between plate electrodes while still retained in the cassette, and samples molecules can be transferred out of the gel strips through the through-holes.

Any lateral movement of the mold inside the cassette can be facilitated by inserting or removing a spacer adjacent to the mold. The spacer can be placed inside the cassette, for example between an edge of the mold and an interior edge (e.g. 212 or 216) of the cassette walls. In some embodiments, a spacer is removed from one side of the mold while another spacer is inserted on the other side of the mold. Before and after movement of the mold, the position of the mold inside the cassette is constrained, so that the windows of the mold are not aligned with the through-holes in the window plates until the spacers are reconfigured. In some embodiments, one or more spacers are wedge-shaped. In some embodiments, an additional through-hole is cut in a cassette wall to accommodate a portion of the mold, such as a portion of one of the window plates, that protrudes through the additional through-hole. The protruding portion can be shaped like a pin or handle for manual manipulation by the end-user, and can slide within the additional through-hole to bring about lateral movement of the mold within the cassette.

Descriptions of related devices and methods, in which portions of the devices can slide past each other to facilitate electrophoresis and electroblotting, are found in co-assigned, U.S. Provisional Application No. 62/067,915, which is incorporated herein by reference.

A notch 217 is carved into the top of one wall of the gel cassette in some embodiments, allowing the practitioner to easily remove the mold from the cassette by pulling on the handle portion 123. Along with the comb and window plates of the mold, the cassette can also accommodate a well layer 219 and a ledge 221. The wells of the well layer can be aligned with the wells 133 of window plate 130 and the teeth of the comb 110, including the indentations 134. The well layer thus provides extra thickness for the wells at the top ends of the lane cavities, so that these wells can accommodate greater volumes of liquid. Such greater volumes are convenient for pouring gel precursor into the lane cavities or pipetting samples into the wells once gel strips are cast in the lane cavities. The ledge 221 can also be aligned to the wells, thereby blocking the wells and preventing liquid from spilling out of the mold or cassette. The wells 133 of window plate 130, together with the well layer 219 and ledge 221, make up an adapter for the mold, as discussed above. In some embodiments, the well layer is treated with adhesive on both sides for attachment to the window plate 130 and ledge 221. However, these pieces can be joined together as desired.

The bottom edges of well layer 219 and ledge 221 can contact the top edge 213 of cassette wall 211 and provide a hard stop when the mold is inserted into the top of the cassette. The well layer and ledge can thus guide insertion and positioning of the mold in the cassette. In these embodiments, the ledge and well layer are not sandwiched between the cassette walls but rather rest on the top edge 213 of the cassette wall 211. The wells and top ends of the lane cavities thus protrude above this edge. The ledge, well layer, window plates and comb can be layered as shown in FIG. 2C for insertion of the mold into the cassette. In some embodiments (see, e.g., FIG. 2B), well layer 219 is omitted and ledge 221 can be bonded directly to window plate 130. Here, the ledge is thick enough to rest on the top edge 213 of cassette wall 211 and prevent further downward movement of the mold into the cassette.

It will be recognized that other approaches, instead of or in addition to those discussed above, can be employed for positioning the mold within the cassette. For example, the mold and cassette can have mechanical protrusions or indentations (e.g., knobs or grooves), in some cases complementary in shape to each other or interlocking, that facilitate or prevent movement of the mold with respect to the cassette in certain directions.

Figure 3A:
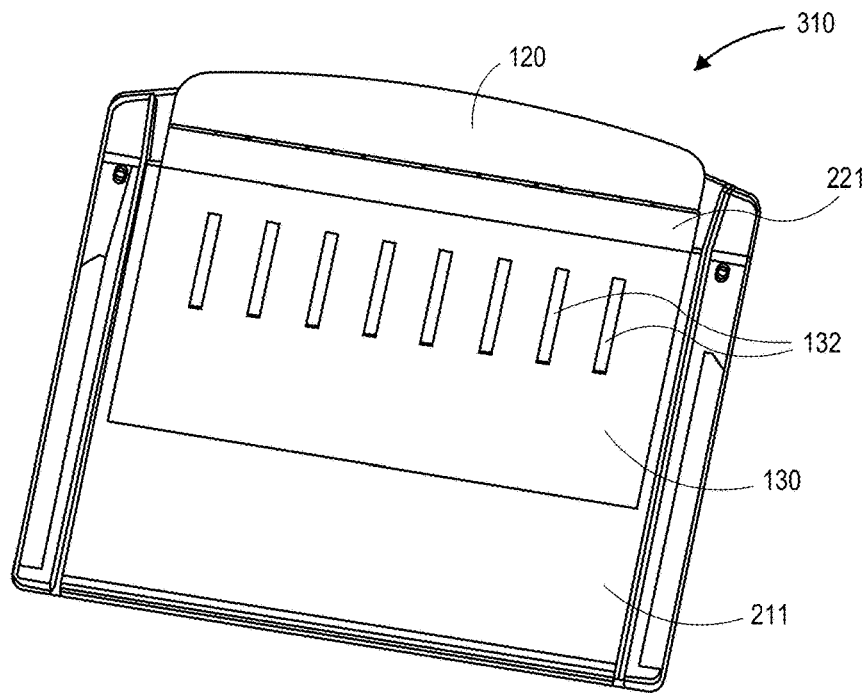
FIGS. 3A and 3B show an assembled mold enclosed in a cassette.
Figure 3B:
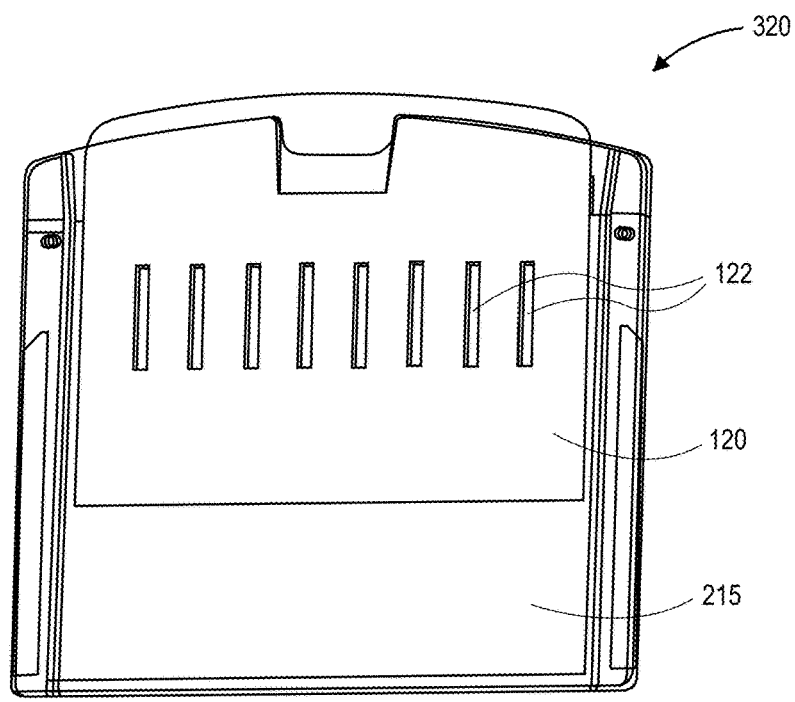

FIGS. 3A-C show the mold fully assembled inside the cassette, with the cassette walls joined together. In FIG. 3A, the window plate 130 faces the viewer and is visible through the transparent cassette wall 211. The comb 110 and most of window plate 120 are occluded by window plate 130. The top ends of the lane cavities, and the well structures formed by the teeth of the comb, window plate 130, and well layer 219, all protrude above the top edge of cassette wall 211 but are occluded by ledge 221. The handle portion 123 of window plate 120 is visible above the other pieces of the mold and the adapter, and in front of window plate 215. In FIG. 3B, window plate 120 faces the viewer and is visible through transparent cassette wall 215. Here, window plate 120 occludes other pieces of the mold and the adapter.

As shown in FIG. 3, the combined thickness of the comb and window plates roughly equals the distance between the interior faces of the cassette walls (~1 mm). As a result, the mold fits snugly inside the cassette. By varying the thickness of the comb, and in turn the distance between the interior faces of the cassette walls, the thickness of gel strips cast inside the mold can be varied. This can affect the dynamics of sample transfer through windows of the mold. The combined thickness of the well layer and ledge roughly equals the thickness of cassette wall 211, so that the exterior face of the ledge visible in FIG. 3A is flush with the exterior face of cassette wall 211.

The cassette shown in FIGS. 2A-C and 3A-C was designed for use with mini slab gels, and is longer, for example between the top 213 and bottom 214 edges of cassette wall 211, than the mold or lane cavities. Alternatively, the cassette and mold can be designed to have comparable lengths.

The windows in the window plates 120, 130 are aligned to each other across each lane cavity, and provide a free passage between the walls 211, 215 of the cassette. When gel strips are cast in the mold, and the mold is enclosed in the cassette, the gel strips fill the lane cavities and emerge through the windows, thus contacting the walls of the cassette. The windows are not as long or wide as the lane cavities to reduce the surface area of contact between the gel strips and walls of the cassette. This reduces friction between the gel strips and walls of the cassette, which can lead to mechanical disruption of the gel strips when the mold is removed from the cassette or slid laterally within the cassette. In some embodiments, the surfaces of the window plates facing the lane cavities are textured to further mitigate this disruption. In other embodiments, detergents or other chemicals are added to the gel precursor, or a coating (e.g., hydrophobic) is applied to the interior surfaces of the walls of the cassette, to reduce friction between the gel strips and the cassette, and to improve sealing. A coating can also be applied to the surfaces of the mold in contact with the walls of the cassette.

Alternatives to the structures, shapes and arrangements shown in FIGS. 1A-C, 2A-C, and 3A-C include the use of lane cavities having round cross-sections, molds made of a single piece of solid material, and windows that extend the entire length of the lane cavities. Further variations in molds that include one-dimensional arrays of lane cavities, and cassettes for accommodating these molds, will be readily apparent to those of skill in the art.

B. Molds Including Two-Dimensional Arrays of Lane Cavities

The array of elongated lane cavities in the mold can also be two-dimensional. For example, the lane cavities can be arranged in the mold in rows or columns. Any configuration of the matrix can be used to achieve such an arrangement, and portions of the matrix surrounding each lane cavity can be connected to each other as desired. Because the lane cavities are oriented parallel to each other, the lane cavities in each row or column can all fall essentially in one plane. When viewed end-on, the lane cavities in each row or column can appear to fall into one line on one face or edge of the matrix, like the lane cavities in a one-dimensional array.

In some embodiments, a mold with a two-dimensional array of lane cavities can be configured to be retained in a microtiter plate. Any number of lane cavities can be present, although in preferred embodiments, this number matches the number of wells used in standard microtiter plates, for example 6, 24, 96, 384, or 1536. In some embodiments, the lane cavities are arranged in a rectangular array, such that the respective numbers of lane cavities in one row and one column have a 2:3 or 3:2 ratio. By also spacing the lane cavities to match the geometries of standard microtiter plates, the mold can be manipulated using pieces of apparatus designed for such plates, such as multi-tipped pipetters, robotic liquid dispensing systems, and robotic plate handlers. The mold can be designed so that the portion of the matrix enclosing each lane cavity can be inserted in one well of a microtiter plate. The microtiter plate can then be used for casting gel strips in the mold, for example to hold the gel precursor in which the mold is submerged.

The mold can also be used in conjunction with a microtiter plate containing electrodes. In such a microtiter plate, each well can contain an electrode disposed on the bottom inside surface, so that electrophoresis can be performed by running current vertically through the well and lane cavity. Alternatively, or in addition, a microtiter plate configured to receive the mold can have two electrodes on the walls of each well, aligned to the windows associated with one lane cavity. These electrodes could be used to transfer sample molecules out of a gel strip retained in the lane cavity after electrophoresis. Depending on the configuration of electrodes, the microtiter plate can thus be used to perform electrophoresis, electroelution/electroblotting, or both. Retaining the mold in a microtiter plate can allow the samples in all lane cavities to be processed simultaneously, or faster than would be possible if the samples were processed one row or column at a time.

In some embodiments, a mold containing a two-dimensional array of lane cavities can be broken into one or more sub-arrays of lane cavities, with each sub-array corresponding to a row of lane cavities in the mold. It will be recognized that assigning lane cavities to a row as opposed to a column is somewhat arbitrary, and that any set of lane cavities arranged more or less in a line can constitute a row. Breaking the mold into sub-arrays allows the lane cavities in each sub-array, and the gel slices they contain, be processed as a group. This can be convenient if, for example, the apparatus used to perform electrophoresis can accommodate the entire mold, but the apparatus used to perform electroelution or electroblotting can accommodate only one sub-array. A breakable mold can also be convenient for casting gel strips in the lane cavities, even if application and manipulation of samples occur after breaking. The mold can be broken at any time, and can include perforations or other structural features to facilitate breaking.

In some embodiments of the breakable mold, some of the windows form internal passages between pairs of lane cavities in adjacent rows. Breaking the mold into one or more sub-arrays bisects these internal passages, and the windows associated with the lane cavities of each sub-array then form passages from the lane cavities to the space outside the sub-array. Constructing the mold this way can be convenient from a manufacturing standpoint, because one hole can be established in the matrix to serve as the windows for two lane cavities in adjacent rows. One piece of the matrix can also be used to separate these lane cavities, rather than using two pieces (each requiring a window hole) separated by a gap. Breaking the mold into sub-arrays allow the windows to pass current for electroelution or electroblotting.

The cassettes described above can also, in some cases, accommodate sub-arrays resulting from breaking a mold with a two-dimensional array of lane cavities. Other cassettes can be envisioned for accommodating full two-dimensional arrays of lane cavities.

Figure 4:
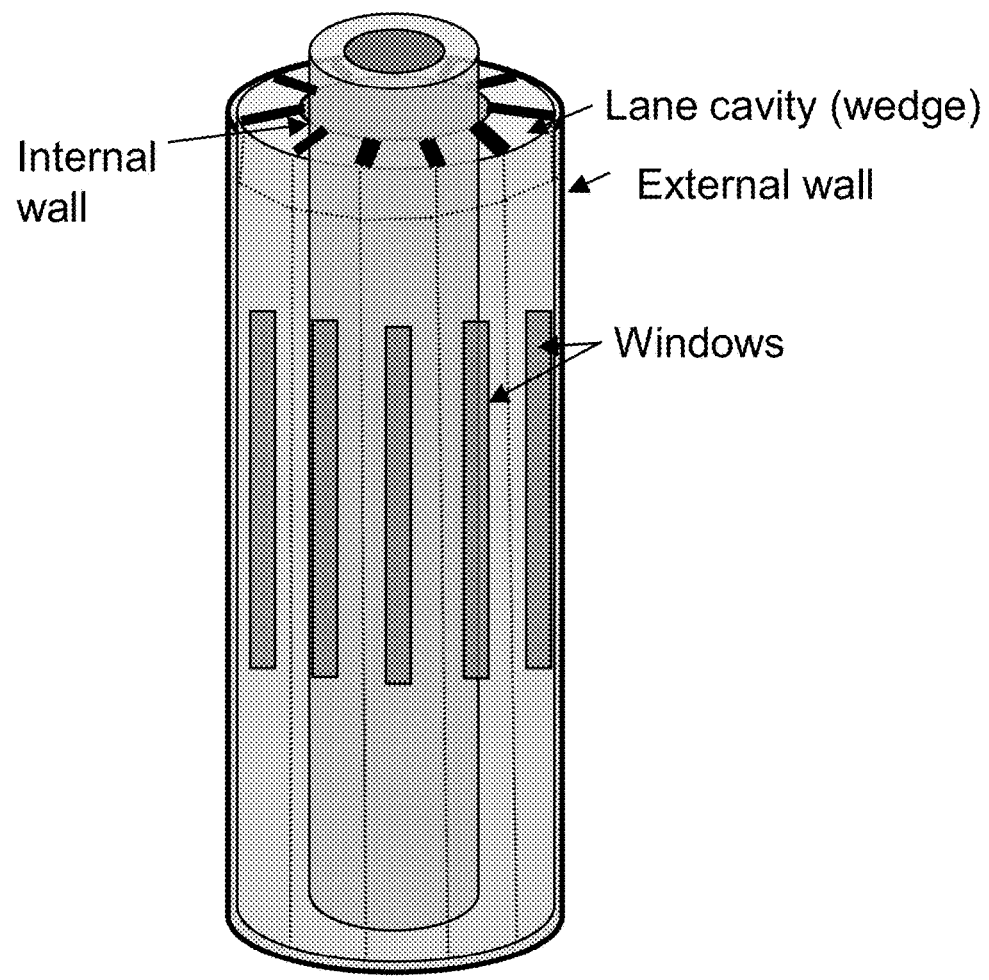
FIG. 4 shows a mold with a two-dimensional array of lane cavities arranged in a circle.

A two-dimensional array of elongated lane cavities can also be prepared with the lane cavities arranged roughly in a circle, as shown in FIG. 4. Here, the matrix has an internal wall and an external wall defining two sides of each lane cavity. The walls are shaped and positioned as concentric cylindrical shells, with each lane cavity occupying a portion or "wedge" of the annular space between the shells. Pieces of solid material segregate the lane cavities from each other and connect the internal and external walls. Windows in the internal wall face each other across the cylindrical space at the center of the mold. Windows in the external wall face outward. Electroelution or electroblotting can be achieved by removing any window covers, placing a single electrode at the center of the mold, and placing one or more electrodes around the periphery of the external wall. Upon applying a potential difference to these electrodes, current can flow through the windows and along radii of the circle in which the lane cavities are arranged. Samples loaded into the lane cavities and separated by electrophoresis can thus be transferred, in a direction orthogonal to the direction of separation, to the space outside the external wall of the matrix. A membrane can be wrapped around the external wall to receive the samples for electroblotting, or strips of membrane can be placed over the windows in the external wall, as discussed below. If desired, the mold can be enclosed in a cassette having a shape complementary to that of the walls of the mold. For example, the cassette can have a tube-like shape and contact the external wall of the matrix. Such a cassette can serve as a window cover for windows in the external wall prior to the transfer of samples.

III. Methods of Separating Analytes and Analyzing Samples

Any of the molds described herein can be used to perform electrophoresis. Generally, gel strips are cast in lane cavities of the mold, and samples are applied to the gel strips. Upon application of a potential difference across the gel strips, and passing a current through the gel strips, sample molecules (also called analytes) migrate through the gel strips at unequal rates and become separated from each other. As will be recognized, many considerations that apply to slab- or capillary-gel electrophoresis also apply to gel-strip electrophoresis using the present molds.

Methods are provided for separating analytes of a sample using a mold as discussed above. The mold retains one or more gel strips. The methods can include the steps of loading a sample onto the first end of an electrophoresis gel strip retained in one lane cavity of the mold; and passing a current through the one lane cavity, between the first and second ends of the gel strip, thereby drawing the sample into the gel strip and separating analytes of the sample by electrophoresis. The first end of the gel strip occurs near the top end of the lane cavity, and the second end of the gel strip occurs near the bottom end of the lane cavity.

The biological sample to be subjected to electrophoresis can be obtained from any source. Examples of potential sources include cells, groups of cells, tissues, or entire organisms, living or dead. The sample can be a cell lysate, tissue homogenate, or sample of blood, saliva, urine, cerebrospinal fluid, or other bodily fluid, among other possibilities. It will be appreciated that samples from different sources vary in the number, identities, and abundances of biological molecules that they contain, and that many of these parameters will not be known at the time the sample is acquired. As is well known, gel electrophoresis can be used to analyze complex biological samples and compare these samples with each other. Comparisons can be made between samples from different biological sources, such as different adult humans, humans of different ages, diseased and healthy humans, humans of different races or ethnicities or from different parts of the world, humans undergoing different treatments for diseases, humans undergoing treatments vs. humans not undergoing treatments, humans vs. non-human mammals, or any variable vs. a control. Other examples will be readily apparent to those of skill in the art. The sample can contain protein, DNA, RNA, or mixtures thereof, and any or all of these kinds of biological molecules can be separated or analyzed using the present methods.

Once obtained, a biological sample may require preparation before it can be run on an electrophoresis gel strip. Such preparation can include, e.g., centrifuging or filtering the sample to remove tissue fragments, membranous structures, or other large contaminants; concentrating the sample into a smaller volume by application of a pressure differential; or adding chemicals to the sample such as protease inhibitors or buffering agents. In particular, in some embodiments the sample is added to or resuspended in a buffer similar to that in which the gel strip is submerged, or from which the gel strip was cast, in terms of pH or salt concentrations. This can ensure that sample molecules will enter the gel strip and migrate within it in an efficient, reproducible manner. Other preparatory steps will be apparent to those skilled in the art. It will be appreciated that some preparatory steps can reduce the number of sample molecules loaded onto the gel strip and ultimately characterized.

The sample can be loaded onto the gel strip as desired, for example using a micropipette. In some embodiments, an adapter or well structure is disposed over the first end of the gel strip, or near the top end of the lane cavity, and can facilitate loading. In some embodiments, the first and second ends of the gel strip are submerged in buffer prior to and during electrophoresis. This provides a conductive path for current to pass between two electrodes and through the gel strip, and can also keep the gel strip hydrated.

A current can be passed through the lane cavity as desired, using established techniques in electrophoresis. A separate pair of electrodes can be placed near the ends of each lane cavity, so that electrophoresis in the lane cavities can be controlled independently, or a single pair of electrodes can be used for all lane cavities. The voltages and currents applied between the electrodes can take on any values, although it will be recognized that the quality of separation achieved during electrophoresis depends on these values. Current can be applied for any length of time. Any power supplies or other apparatus can be coupled to the electrodes and used to apply the current.

Analytes that are loaded onto the gel strip can be visualized during or after electrophoresis. Visualization during electrophoresis can be accomplished by making reference to a tracking dye, such as xylene cyanol or bromophenol blue, that is loaded onto the gel strip and migrates through the gel strip along with the sample. Alternatively or in addition, a stained marker, such as a protein or nucleic acid molecule bearing a fluorescent or colored moiety, can be added to the sample and followed during electrophoresis. Preferably, the stained marker (e.g., a standard) has a known weight or charge, and migrates through the gel strip at a predictable rate. Markers loaded onto different gel strips can be used to determine whether analytes migrate through the gel strips at different rates, and align the gel strips with each other. Another alternative is to directly stain molecules of the sample, such as by covalently coupling molecules bearing a reactive chemical group to a colored moiety.

In some embodiments, analytes of the sample are visualized through one of the windows associated with the one lane cavity retaining the gel strip. This is feasible if any coverings over the window, such as the cassette walls discussed above, are minimally translucent or transparent. Visualization during electrophoresis allows the practitioner to gauge the rate at which analytes are migrating through the gel strip, and/or identify whether an analyte of interest is present in the sample.

Visualization of analytes after electrophoresis can be accomplished using the methods described above, or using other standard methods, reviewed for example in Sambrook and Russell, *Molecular Cloning: A Laboratory Manual* ($3^{rd}$ ed.), New York: Cold Spring Harbor Laboratory Press, 2001. First, the windows of the mold can be uncovered, for example by removing the mold from a cassette, thereby exposing the gel strip to any buffer in which the mold is submerged. Analytes in the gel strip can then be made visible by dissolving a staining agent in this buffer. Examples of staining agents include Coomassie Brilliant Blue, SYPRO Ruby, and ethidium bromide. It will be recognized that an appropriate staining agent must be chosen for the particular types of biological molecules present in the sample, and that visualization can also be achieved by means other than staining. Conveniently, analytes can be visualized through the windows of the mold, without removing the gel strip from the mold.

Protein analytes in particular can be visualized after electrophoresis using stain-free chemistry. Conveniently, some of these embodiments do not require uncovering windows of the mold or otherwise exposing the gel strip to the space outside the mold. According to these embodiments, a halo-substituted organic compound is incorporated into the gel strip and is in contact with proteins that have been separated by electrophoresis. Exposure of the gel strip to UV radiation induces a reaction between the halo-substituted organic compound and tryptophan residues of the proteins. The reaction covalently modifies the tryptophan residues and renders them fluorescent, such that the residues are excitable with UV light and emit in the visible range. Thus, proteins in the gel strip can be detected upon prolonged or repeated exposure of the gel strip to UV light. Examples of suitable halo-substituted organic compounds, also called 'haloalkanes' in the art, are trichloro compounds such as chloroform, trichloroacetic acid, and trichloroethanol. One or more halo-substituted organic compounds can be incorporated into a gel strip at the time it is formed in the mold, as components of the gel precursor. A halo-substituted organic compound can also be incorporated into a gel strip subsequently, for example by incubating a gel strip in a solution containing the compound and allowing the compound to diffuse into the gel strip. Stain-free detection can be used to quantify and/or normalize the amounts of proteins (for example, particular proteins or all proteins) within samples and between samples. Further disclosure of stain-free protein quantification and normalization is found in co-assigned, co-pending U.S. patent application Ser. No. 13/870,710, which is incorporated herein by reference.

In some embodiments, the lane cavity retaining the gel strip is part of a one-dimensional array of lane cavities, and the windows associated with each lane cavity in this array form passages from the lane cavity through the matrix to the space outside the mold. Here, the methods can also include transferring analytes out the gel strip retained in one lane cavity. First, after electrophoresis, any sealant or window covers over the windows associated with the one lane cavity are removed. This can involve removing the mold from a cassette retaining the mold, or shifting the mold within the cassette to align the windows with through-holes in the cassette walls. Next, current is passed through the windows associated with the one lane cavity, in a direction orthogonal to that used for electrophoresis, thereby transferring analytes out the gel strip. The analytes can be transferred without having to break open the mold or handle the gel strips.

Current can be applied in the orthogonal direction as desired, using electrodes positioned on opposite sides of the lane cavity and near the windows associated with the lane cavity. As for electrophoresis, individual pairs of electrodes can be used for each lane cavity, or one pair of electrodes (e.g., plate electrodes) can be used for all lane cavities. Any desired currents, voltages, and power supplies can be used.

In some cases the analytes are transferred to the surface of the gel strip in a technique called electroelution. The analytes can then be collected by, for example, washing the gel strip in a buffer and collecting the buffer. This can be done while the gel strip is still retained in the lane cavity. Variations of electroelution are known to those of skill in the art.

In some cases, in a technique called electroblotting, the analytes are transferred to a membrane formed of nitrocellulose, nylon, polyvinyl difluoride, or similar materials. The analytes are transferred directly between the gel strip and membrane through one of the windows associated with the lane cavity that retains the gel strip. The membrane is placed near this window prior to passing current through the window. Various kinds of electroblotting are known and practiced in the art. When the analytes are DNA fragments, the transfer is termed a Southern blot after its originator, the British biologist Edwin M. Southern. By analogy, the transfer of RNA fragments is termed northern blotting, and the transfer of proteins or polypeptides is termed western blotting. Still further examples are "eastern" blots for post-translational modifications, and "far western" blots for protein interactions. All kinds of electroblotting are within the scope of the present methods.

Electroblotting can be performed in either a wet, dry, or semi-dry format. In wet blotting, the gel strip and membrane are layered over each other in a stack, which is immersed in a transfer buffer solution in a tank on whose walls are mounted wire or plate electrodes. The electrodes are then energized to cause the solutes to migrate from the gel strip to the membrane. In semi-dry blotting, filter papers wetted with the transfer buffer solution are placed on the top and bottom of the stack with the gel strip and the membrane in between to form a "blotting sandwich." The electrodes are then placed in direct contact with the exposed surfaces of the wetted filter papers. In dry electroblotting, no liquid buffer is used other than that residing in the gel strip. Descriptions of wet, dry, and semi-dry electroblotting and the associated materials and equipment are found in Margalit et al. (Invitrogen) United States Patent Application Publications No. US 2006/0272946 A1 (Dec. 7, 2006), No. US 2006/0278531 A1 (Dec. 14, 2006), and No. US 2009/0026079 A1 (Jan. 29, 2009); Littlehales (American Bionetics) U.S. Pat. No. 4,840,714 (Jun. 20, 1989); Dyson et al. (Amersham International) U.S. Pat. No. 4,889,606 (Dec. 26, 1989); Schuette (Life Technologies, Inc.), U.S. Pat. No. 5,013,420 (May 7, 1991); Chan et al. (Abbott Laboratories), U.S. Pat. No. 5,356,772 (Oct. 18, 1994); Camacho (Hoefer Scientific Instruments), U.S. Pat. No. 5,445,723 (Aug. 29, 2005); Boquet (Bertin & Cie), U.S. Pat. No. 5,482,613 (Jan. 9, 1996); and Chen (Wealtec Enterprise Co., Ltd.) U.S. Pat. No. 6,592,734 (Jul. 15, 2003). All of these kinds of electroblotting can be performed with the gel strip retained in the lane cavity of the mold.

Regardless of the electroblotting format, the membrane is often treated with detection reagents after transfer to render analytes on the membrane detectable. These detection reagents can be binding partners for the analytes. In Southern and northern blots, for example, the detection reagents are hybridization probes followed by a fluorescent or chromogenic dye. In western blots, the detection reagents are antibodies followed by the use of conventional labeling techniques to detect the antibodies. Similar or analogous procedures, known among skilled biochemists, are performed with far western blots and eastern blots.

In some embodiments, strips of membrane are cut to fit over each window of the mold. Each membrane strip can thus receive analytes from a single gel strip. The membrane strips can be treated individually, for example incubated with different detection reagents. This arrangement allows smaller volumes of detection reagents to be used and different kinds of analytes to be detected in one experiment. Using membrane strips can also preserve information about the positions of samples loaded onto gel strips in the mold, and facilitate automation. In some embodiments, antibodies or other detection reagents are delivered to the membrane strips using a porous substrate (e.g., paper), on which the detection reagents are printed. This delivery method is described, for example, in co-pending, co-assigned U.S. patent application Ser. Nos. 13/950,590 and 14/340,364. Pieces of the substrate can be cut to have the same sizes as the membrane strips.

In embodiments where the mold fits inside a cassette, and through-holes are cut in the cassette walls to align with the windows of the mold, each membrane strip can be cut to fit inside a through-hole, or cover a through-hole at the interface between the mold and cassette wall. A membrane strip can be brought into contact with a gel strip by sliding the mold laterally within the cassette as described above. A set of membrane strips can also be prepared as a card, with the card having indentations complementary in shape and spacing to the through-holes. The card can be pressed against the exterior of the cassette during electroblotting such that the indented portions fit inside the through-holes and are available to receive analytes from the gel strips in the mold. If the membrane strips are part of the same card, or are otherwise physically coupled together, they can be conveniently handled for treatment with detection reagents.

Molds with two-dimensional arrays of lane cavities can also be used in the present methods. When the mold is configured to be broken into one or more sub-arrays of lane cavities, each sub-array corresponding to a row of lane cavities, then the method further includes breaking the mold, such that one of the sub-arrays contains one lane cavity of interest. A sample can be loaded onto a gel strip retained in the one lane cavity, as described above, and electrophoresis can be performed. If the windows associated with this lane cavity form passages from the lane cavity through the matrix to the space outside the mold, then electroelution or electroblotting can also be performed subsequently. As is the case for molds containing one-dimensional arrays of lane cavities, the methods can include the step of removing any sealant or window covers over the windows associated with the lane cavity of interest. This step can involve removing the sub-array from a cassette retaining the sub-array.

The present methods can also include the step of forming an electrophoresis gel strip in one lane cavity of the mold, for example the lane cavity of interest, prior to carrying out electrophoresis. This can be done by submerging the mold in gel precursor and allowing the gel strip to solidify in the lane cavity, as described above. Alternatively, the gel strip can be formed by pouring gel precursor into the lane cavity and allowing the gel strip to solidify. In some embodiments, one or more gel strips are formed while the mold is retained in a cassette. In embodiments that include a cassette with through-holes cut in the cassette walls, one or more removable gaskets, made of rubber, foam, or the like, can be inserted in the through-holes. The gaskets can prevent leakage when lane cavities of the mold are filled with gel precursor, and optionally can be left in place during electrophoresis. Variations on these methods will be apparent to those of skill in the art.

IV. Systems for Performing Electrophoresis, Electroelution, and Electroblotting

The present application also provides systems for performing electrophoresis, electroelution, and electroblotting using the molds and methods described above.

One such system includes a cassette for retaining a mold, as well as a first electrode and a second electrode. The cassette and electrodes are arranged to facilitate electrophoresis using the mold. The electrodes are of opposite polarity, and are positioned to drive current through one or more gel strips retained in lane cavities of the mold. Specifically, the first electrode is positioned near the top end of a lane cavity of the mold when the mold is retained in the cassette, and the second electrode is positioned near the bottom end of the lane cavity when the mold is retained in the cassette.

Another system can be used with a mold having a one-dimensional array of elongated lane cavities, where the windows associated with each lane cavity form passages from the lane cavity through the matrix to the space outside the mold. Here, the system includes a cassette for retaining such a mold, as well as a first separation electrode, a second separation electrode, a motor, a first transfer electrode, and a second transfer electrode. The first and second separation electrodes are positioned near the top and bottom ends, respectively, of a lane cavity of the mold when the mold is retained in the cassette. These electrodes are of opposite polarity and are used for electrophoresis. The first and second transfer electrodes are also of opposite polarity and are used for electroelution or electroblotting. To make use of the transfer electrodes, the mold must be removed from the cassette and the location in which electrophoresis occurs. Accordingly, the motor is configured to remove the mold from the cassette and place the mold in proximity to the first and second transfer electrodes. With the mold relocated, the first and second transfer electrodes are positioned on opposite sides of the lane cavity, near the windows associated with the lane cavity.

In some embodiments of these systems, when the mold is retained in the cassette, the cassette contacts the matrix of the mold and is aligned to the windows associated with the lane cavity, thereby preventing substances or current from passing through the windows associated with the lane cavity. The cassette therefore allows electrophoresis to occur, but not electroelution or electroblotting.

The mold, cassette, electrodes, and other components of these systems can make use of any support structures useful for achieving the specified relationships among the components. For example, the cassette can be held in a gel electrophoresis cell that places the electrodes near the mold as described. Other materials and apparatus, for example buffers, power supplies, and liquid dispensing systems, can be incorporated into these systems as desired.

V. Examples

A. Example 1. Electrophoresis and Electroblotting of Colored Protein Standards

A mold was constructed according to one embodiment of the invention. The mold included eight elongated lane cavities arranged in a one-dimensional array; a matrix separating the lane cavities from each other and from the space outside the mold; and a plurality of windows, wherein two windows were associated with each lane cavity and disposed on opposite sides of the lane cavity, each window running lengthwise along the lane cavity and penetrating the matrix, thereby forming a passage from the lane cavity through the matrix to the space outside the mold.

Figure 5:
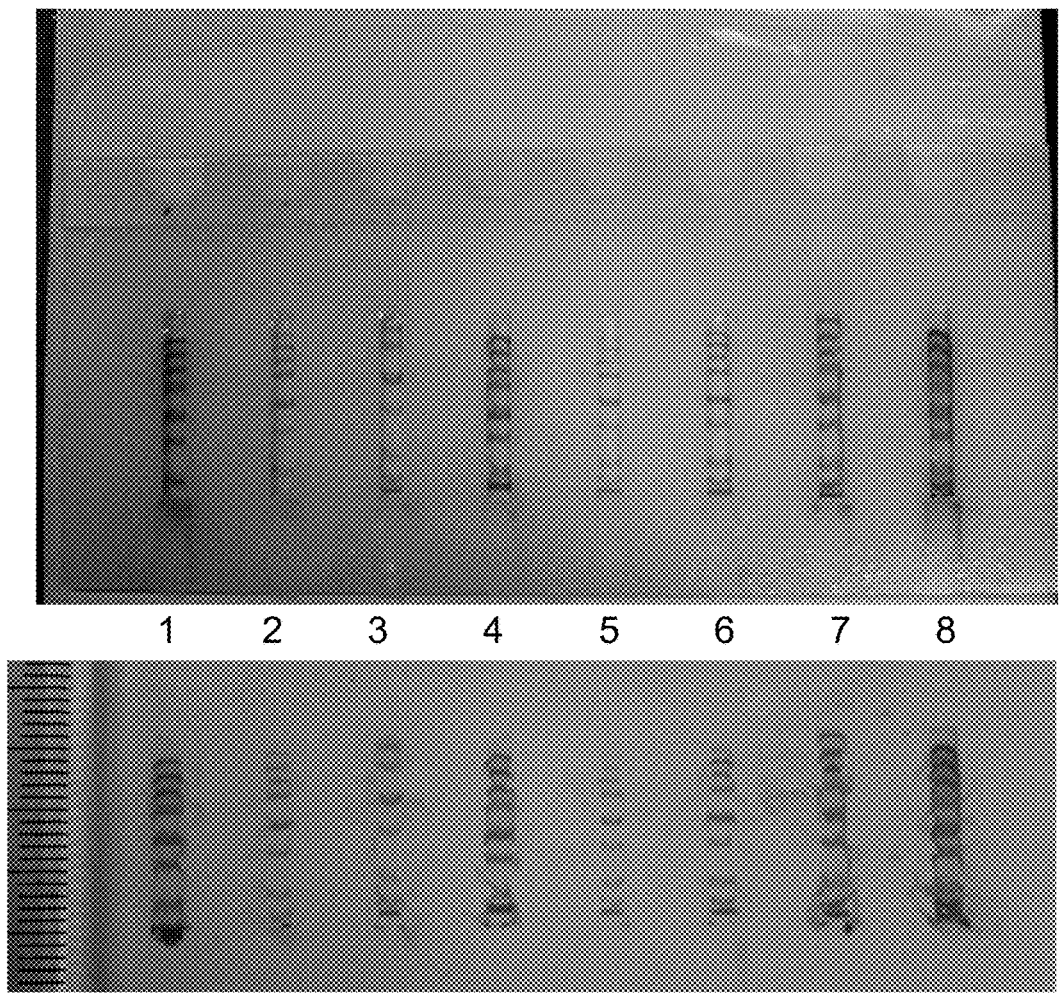
FIG. 5 shows electrophoretic separation and electroblotting of colored protein standards according to Example 1.

8% polyacrylamide gel strips were cast in lane cavities of the mold, and different volumes of Precision Plus Protein™ Dual Color standards (Bio-Rad Laboratories, Inc., Hercules, Calif., USA) were loaded onto the gel strips while the mold was enclosed in a cassette. Proteins of the standards were separated by electrophoresis and subsequently visualized while the gel strips were retained in the mold (FIG. 5, top).

After removing the mold from the cassette, a nitrocellulose membrane was placed in proximity to the mold and a current was passed through windows of the mold. Proteins were transferred through the windows and onto the membrane by electroblotting using a Trans-Blot Turbo apparatus (Bio-Rad). Proteins were then visualized on the membrane (FIG. 5, bottom). Comparison of the top and bottom portions of FIG. 5 shows that the proteins were efficiently transferred from the gel strips to the membrane.

B. Example 2. Western Blotting of Proteins from HeLa Lysate

A mold was constructed according to one embodiment of the invention, as in Example 1. Polyacrylamide gel strips were cast in lane cavities of the mold, and HeLa lysate samples were loaded in duplicate onto the strips in amounts of 2, 4, and 8 micrograms (two strips per amount of protein). Proteins in the samples were separated by electrophoresis and transferred to a nitrocellulose membrane as in Example 1. The membrane was then cut in half and probed with two different antibodies.

Figure 6:
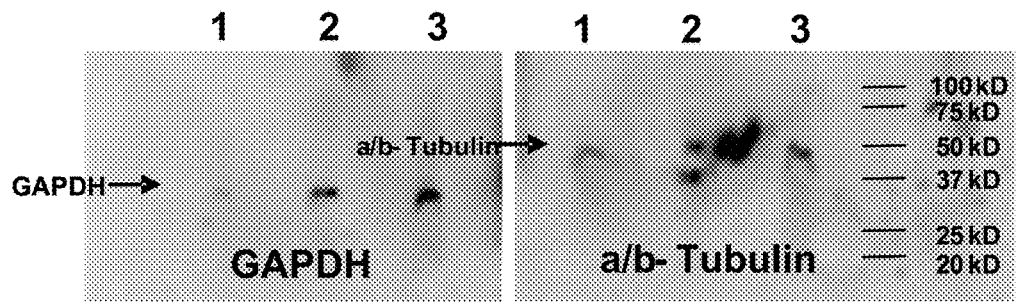
FIG. 6 shows western blotting of HeLa lysate proteins according to Example 2.

One half of the membrane was probed with a 1:1000 dilution of rabbit primary antibody raised against GAPDH. A secondary antibody (goat anti-rabbit-HRP conjugate) was then applied at a 1:5000 dilution, and proteins were detected using the Clarity chemiluminescent substrate (Bio-Rad) (FIG. 6). The other half of the membrane was probed with a 1:1000 dilution of rabbit primary antibody against a/b-tubulin. Proteins were detected on this half of the membrane using the same secondary antibody and chemiluminescent substrate (FIG. 6).

In the claims appended hereto, the term "a" or "an" is intended to mean "one or more." The term "comprise" and variations thereof such as "comprises" and "comprising," when preceding the recitation of a step or an element, are intended to mean that the addition of further steps or elements is optional and not excluded.

All documents (for example, patents, patent applications, books, journal articles, or other publications) cited herein are incorporated by reference in their entirety and for all purposes, to the same extent as if each individual document was specifically and individually indicated to be incorporated by reference in its entirety for all purposes. To the extent such documents incorporated by reference contradict the disclosure contained in the specification, the specification is intended to supersede and/or take precedence over any contradictory material.

Many modifications and variations of this invention can be made without departing from its spirit and scope, as will be apparent to those skilled in the art. The specific embodiments described herein are offered by way of example only and are not meant to be limiting in any way. It is intended that the specification and examples be considered as exemplary only, with the true scope and spirit of the invention being indicated by the following claims.

What is claimed is:

1. A mold for casting and retaining electrophoresis gel strips, the mold comprising:
  an array of elongated lane cavities, each having a length greater than a width, each lane cavity having a top end, a bottom end, and two or more sides disposed along the length of the lane cavities, the lane cavities oriented parallel to each other;
  a matrix comprising at least one solid material and disposed along the sides of the lane cavities, the matrix separating the lane cavities from each other and from a space outside the mold; and
  a plurality of windows, wherein two windows are associated with each lane cavity and are disposed on opposite sides of the lane cavity orthogonal to the length of the lane cavities, each window running lengthwise along the lane cavity and penetrating the matrix, wherein:
  the windows associated with each lane cavity form passages from the lane cavity through the matrix to the space outside the mold,
  the matrix comprises a first solid material sandwiched between two pieces of a second solid material, the first solid material separating the lane cavities from each other, and the two pieces of the second solid material at least partially separating the lane cavities from the space outside the mold,
  the first solid material comprises a comb, the comb comprising a plurality of teeth, and the lane cavities comprise the spaces between the teeth, and the second solid material comprises two window plates, the window plates bonded to opposite sides of the comb, and each window plate comprising at least one of the plurality of windows, thereby forming an opening from each lane cavity through the matrix to an adjacent lane cavity or the space outside the mold.

2. A kit comprising:

the mold of claim 1, and a cassette that retains the mold when the mold is inserted into the cassette, wherein the cassette contacts the matrix of the mold and is aligned to a window associated with at least one lane cavity, thereby preventing substances or current from passing through the window associated with the at least one lane cavity.

3. The mold of claim 1, wherein the windows run the entire length of the lane cavities.

4. The mold of claim 1, wherein the windows are as wide as associated lane cavities.

5. The mold of claim 1, wherein the windows have different widths along the length of associated lane cavities.

* * * * *